(12) United States Patent
Roth

(10) Patent No.: US 11,564,828 B2
(45) Date of Patent: Jan. 31, 2023

(54) MOUTH GUARD TO PREVENT TEETH GRINDING, JAW CLENCHING AND TMJ

(71) Applicant: Karen Roth, Hillsdale, NJ (US)

(72) Inventor: Karen Roth, Hillsdale, NJ (US)

( * ) Notice: Subject to any disclaimer, the term of this patent is extended or adjusted under 35 U.S.C. 154(b) by 30 days.

(21) Appl. No.: 16/183,925

(22) Filed: Nov. 8, 2018

(65) Prior Publication Data

US 2020/0146873 A1 May 14, 2020

(51) Int. Cl.
*A61F 5/00* (2006.01)
*A61F 5/56* (2006.01)

(52) U.S. Cl.
CPC ........ *A61F 5/566* (2013.01); *A61F 2005/563* (2013.01)

(58) Field of Classification Search
CPC ...... A61F 5/566; A61F 2005/563; A61F 5/37; A61F 5/56; A63B 71/085; A61C 5/14; A61C 7/08; A61C 7/36
USPC ........................................................ 128/861
See application file for complete search history.

(56) References Cited

U.S. PATENT DOCUMENTS

| | | | | |
|---|---|---|---|---|
| 3,223,085 A * | 12/1965 | Gores | ................ | A63B 71/085 128/861 |
| 5,899,691 A * | 5/1999 | Parker | ................ | A63B 23/032 433/6 |
| 6,530,375 B1 * | 3/2003 | Cieslik, Jr. | ............. | A61F 5/566 128/859 |
| 7,607,438 B2 * | 10/2009 | Pelerin | ................ | A61F 5/566 433/7 |
| 7,654,267 B2 * | 2/2010 | Boyd | ................ | A61F 5/566 128/859 |
| 8,459,267 B2 * | 6/2013 | Zimmerman | ........ | A63B 71/085 128/861 |
| 9,681,978 B1 * | 6/2017 | Roth | ................ | A61F 5/56 |
| 10,080,680 B2 * | 9/2018 | Magness | ................ | A61F 5/566 |
| 10,500,083 B1 * | 12/2019 | Boyd | ................ | A61F 5/05891 |
| 2006/0021622 A1 * | 2/2006 | Buffington | ............. | A61F 5/566 128/861 |
| 2009/0223526 A1 * | 9/2009 | Berghash | ............. | A63B 71/085 128/861 |
| 2012/0090625 A1 * | 4/2012 | Evans | ................ | A63B 71/085 128/861 |
| 2015/0000677 A1 * | 1/2015 | Magness | ................ | A61F 5/566 128/861 |

* cited by examiner

*Primary Examiner* — Adam Baker

(57) ABSTRACT

The new and improved mouth guard of the invention comprises a flexible mouth guard having a channel for one's teeth and an integral flexible bubble that protrudes from the upper or lower front teeth. The bubble is positioned around and under the upper two to four front teeth or around and above the lower two to four front teeth. The flexible bubble preferably of flexible polymer or plastic material prevents the upper and lower posterior teeth from engaging thereby preventing the clenching and grinding of bruxism. The multiple bubbles absorb shock and assists in preventing trauma and dental issues.

4 Claims, 5 Drawing Sheets

MOUTH GUARD TO PREVENT TEETH GRINDING, JAW CLENCHING AND TMJ

CROSS REFERENCE TO RELATED APPLICATIONS

This application claims the benefit of U.S. Provisional Application Ser. No. 62/761,368 filed Mar. 21, 2018 which is incorporated herein by reference in its entirety. The provisional application is entitled Flexible Bubble Mouth Guard for the Prevention of Teeth Grinding and Clenching.

STATEMENT REGARDING FEDERALLY SPONSORED RESEARCH OR DEVELOPMENT

Not Applicable

PARTIES TO A JOINT RESEARCH AGREEMENT

Not Applicable

FIELD OF THE INVENTION

This invention relates to the field of mouth guards and in particular to devices for preventing bruxism involving teeth grinding and related problems such as TMJ.

BACKGROUND OF THE INVENTION

This invention is intended to alleviate and possibly eliminate the problems associated with teeth clenching, grinding and TMJ as discussed in applicant's U.S. Pat. No. 9,681,978. Bruxism is excessive grinding of the teeth and/or excessive clenching of the jaw and is recognized as a serious problem which can lead to even more serious health issues. It is also important to provide a mouth guard to protect teeth from injury in sports where clenching is common and shocks often occur. Having a soft flexible, elastic customized mouth guard with an integral bubble encourages use of the device and prevents damage to the teeth.

DESCRIPTION OF RELATED ART INCLUDING INFORMATION DISCLOSED UNDER 37 CFR 1.97 & 1.98

The prior art includes the following patents:

U.S. Pat. No. 9,681,978 by applicant discloses a mouth guard for the prevention of jaw clenching and teeth grinding. The mouth guard discloses a tab disposed between a person's top and bottom teeth to resist full closure of the jaws so the upper and lower back teeth do not engage each other. The patent discloses several embodiments with variations on the bruxism preventing tab.

U.S. Pat. No. 6,675,806 to Kittelsen, et al, discloses a composite force absorbing mouth guard with elastomeric traction pads on the bottom of the mouth guard. A hard reverse bite plate wedge is thicker towards the rear of thereof to place the lower jaw in an optimum position to prevent nerve impingement as well as spacing the upper and lower jaws apart.

U.S. Pat. No. 8,205,618 to Berghash discloses a sports mouth guard of a three laminate construction. The mouth guard includes an upper portion with holes in a channel floor and lower platform with posts aligned to fit into the holes providing a protective cushion U.S. Pat. No. 9,968,419 to Alverez, et al, discloses an appliance for preventing bruxism with protuberances and also for improving air intake.

The relevant prior art noted above does not disclose or anticipate the flexible bubble appliance feature of applicant's invention.

SUMMARY OF INVENTION

The present invention relates to mouth guards and in particular to a soft flexible elastic mouth guard of various materials such as silicone rubber, or ultra-low density polyethylene designed to cover and protect a person's upper or lower teeth. The mouth guard also includes a flexible bubble or air filled spherical cavity that protrudes from the upper or lower surface of the mouth guard. The flexible bubble is positioned around and under the upper two to four front teeth or alternatively, around and above the lower front two to four teeth to prevent the posterior teeth from touching and absorbing tension when biting thus preventing clenching and grinding.

Accordingly, it is an object of this invention to provide a new and improved mouth guard to eliminate the problems associated with teeth clenching and grinding It is another object of this invention to provide a new and improved form fitting mouth guard which combats bruxism and sports injuries.

It is a more specific object of this invention to provide an easy to manufacture, new and improved flexible mouth guard having a formed bubble portion which protrudes from the upper or lower surface of the mouth and is placed around the front teeth to prevent clenching and grinding.

It is a further object of this invention to provide a new and improved mouth guard to prevent bruxism or dental issues having a plurality of spaced shock absorbing flexible bubbles extending outwardly from a channeled tray to engage the opposite set of teeth.

BRIEF DESCRIPTION OF DRAWINGS

The above and other objects of this invention may be more clearly seen when viewed in conjunction with the accompanying drawings wherein.

DETAILED DESCRIPTION OF THE INVENTION

Figure 1:
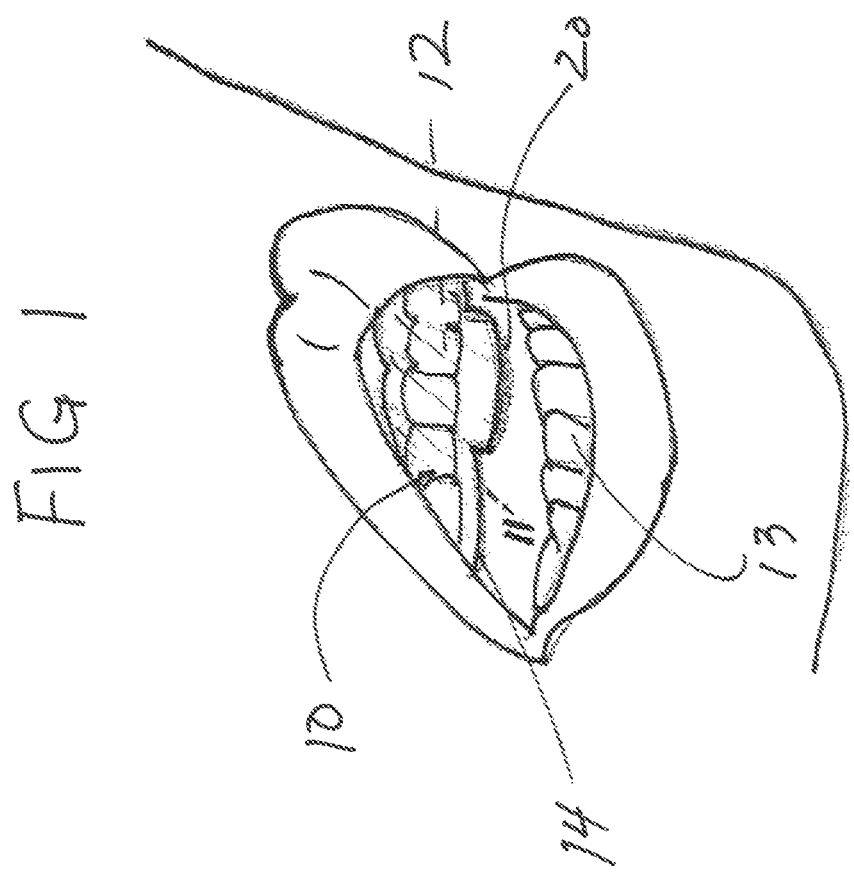
FIG. 1 shows a perspective view of the mouth guard bubble placed around and under the upper front two to four teeth in a mouth.
Figure 2:
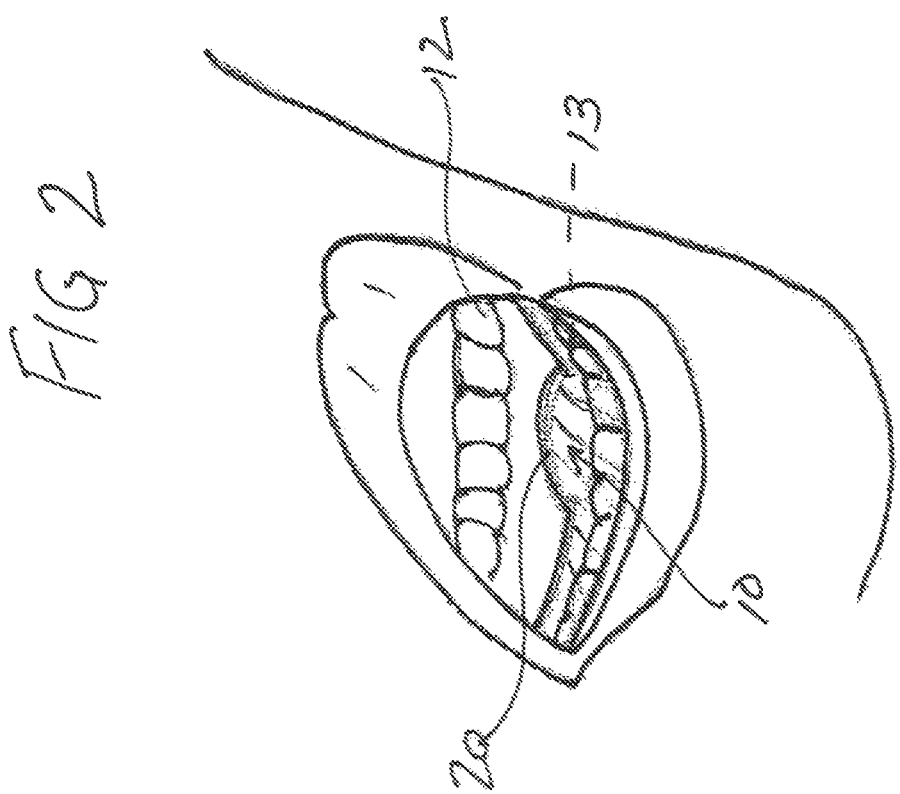
FIG. 2 shows the mouth guard bubble positioned around and above the lower two to four front teeth in a perspective view in a mouth.

Referring now to the drawings and particularly FIGS. 1 and 2, the invention comprises a mouth guard 10 which can be worn day or night to prevent teeth clenching, grinding and TMJ. The mouth guard 10 is sized and configured in a substantially U-shape tray having a channel 11 to encompass a person's upper 12 or lower teeth 13. The mouth guard 10 further includes an integral flexible bubble 20 or air filled spherical cavity at the base 14 of the U-shape where the front teeth are located. The integral design of the bubble 20 makes the mouth guard 10 easy to manufacture compared with mouth guards having tabs and protrusions of various types.

The flexible bubble 20 protrudes from the upper or lower surface of the mouth guard 10 depending on whether it is affixed to the upper 12 or lower teeth 13. The flexible bubble 20 can be placed around and under the upper two to four front teeth as shown in FIG. 1 Alternatively, the mouth guard 10 may be positioned on the lower teeth 13 and the flexible bubble 20 can be positioned around and above the front two to four teeth as shown in FIG. 2

Figure 5:
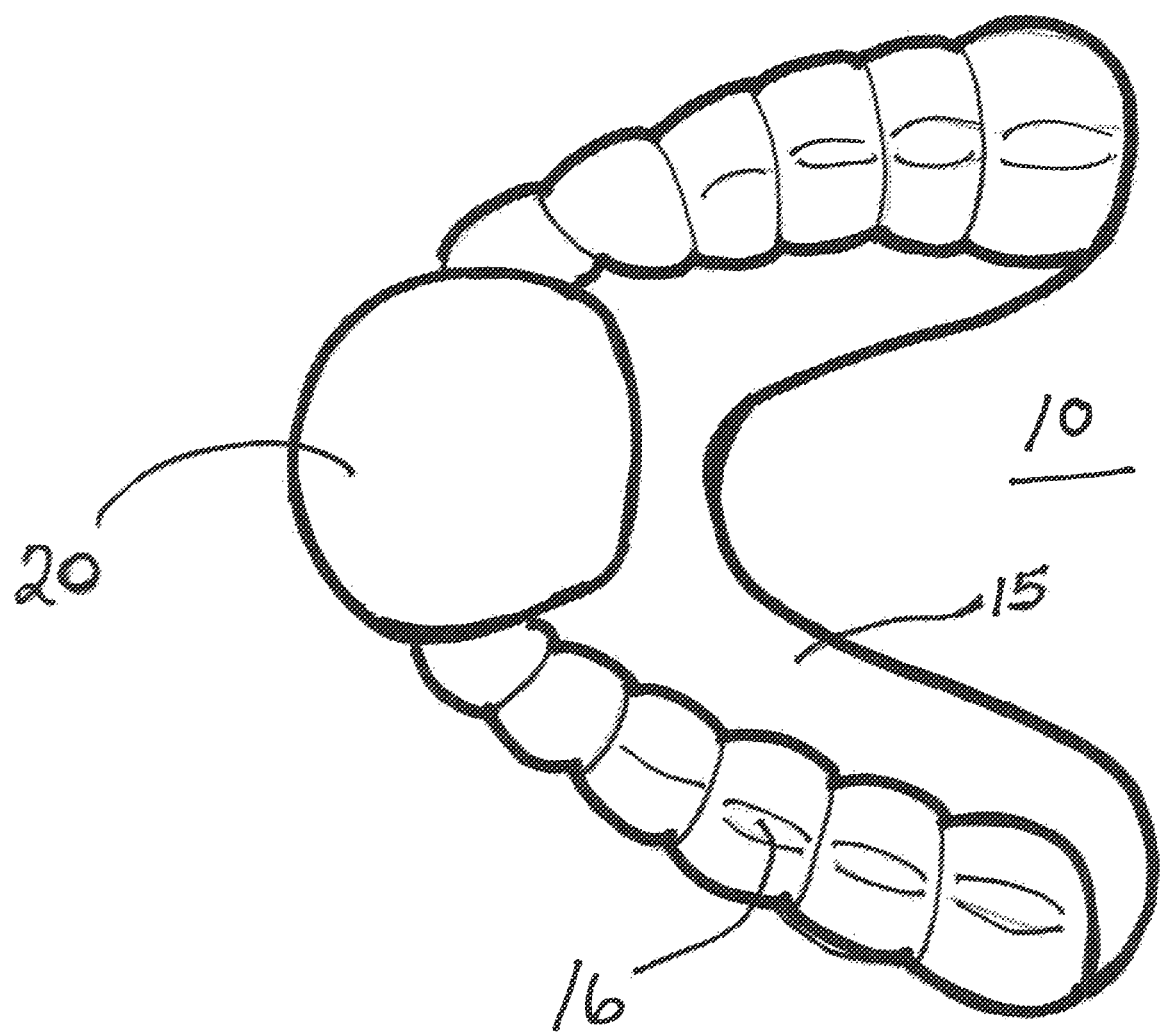

The purpose of the mouth guard 10 with the protruding flexible bubble 20 around either the upper 12 or lower 13 front teeth is to prevent the front teeth from touching and absorbing tension when biting thus preventing clenching and grinding FIG. 5 is a plan view of the mouth guard 10 from the bottom thereof showing the tray 15 and the bubble 20 protruding therefrom. The tooth prints 16 are shown in the channel 11 of flexible elastic material which molds to an individual's teeth. The bubble 20 which prevents bruxism is prominently shown in the front of the mouth guard 10 where it engages the opposite teeth.

Figure 3:
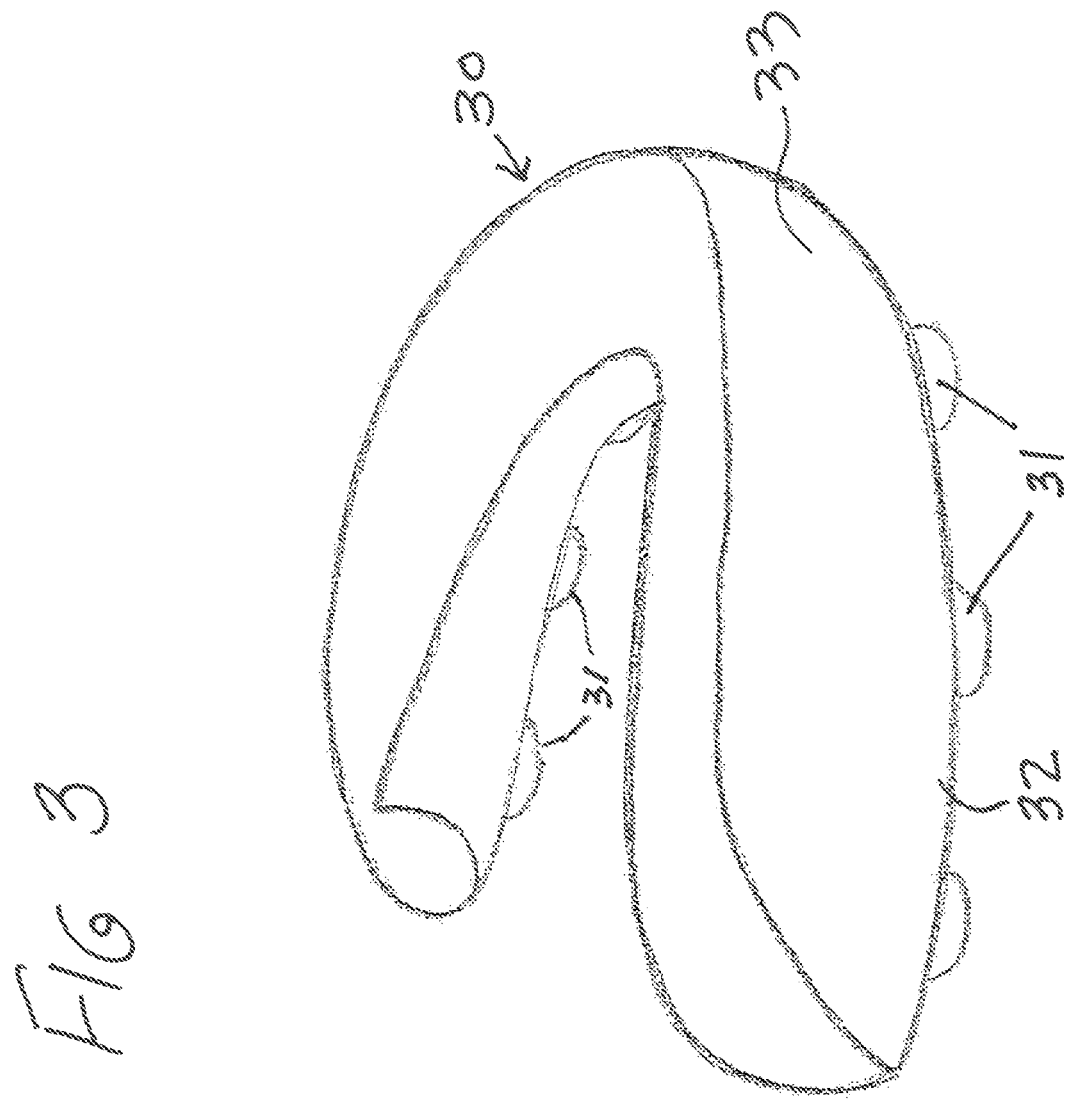
FIG. 3 shows the mouth guard worn over upper teeth with a plurality of spaced flexible bubbles around and under a few or many teeth.
Figure 4:
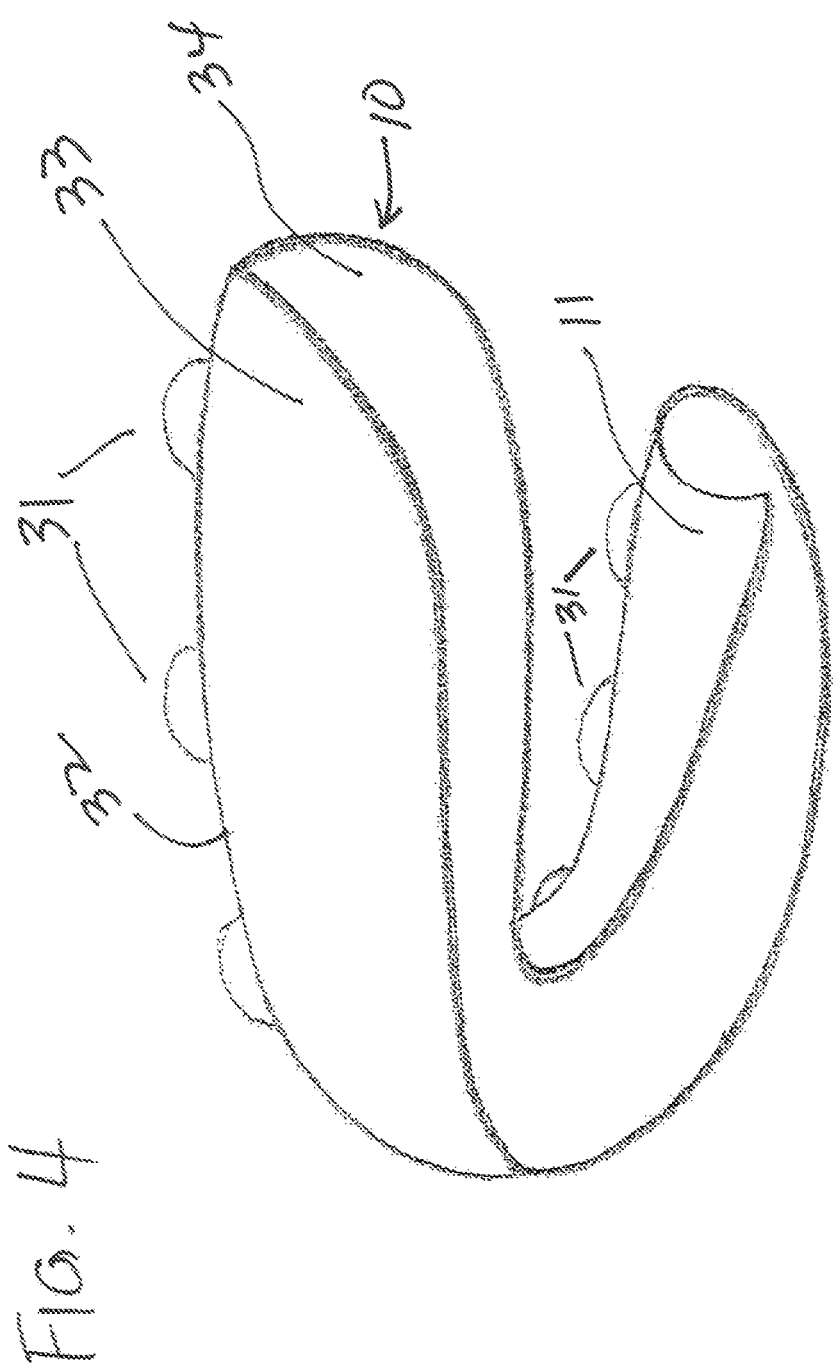
FIG. 4 shows in a perspective view a mouth guard worn over bottom teeth with a plurality of flexible bubbles positioned around and above a few or many teeth; and, FIG. 5 is a plan view of the bubble mouth guard from the bottom thereof.

In alternate embodiments, as shown in FIGS. 3 and 4, the mouth guard 30 is not limited to one protruding flexible bubble 20 on or around the front teeth of either upper 12 or lower 13 set of teeth. The invention can also comprise of a series of spaced protruding bubbles 31 extending from the base of the tray 33 beneath a few or many upper teeth 12 in the channel as shown in FIG. 3. Alternatively, the bubbles 31 may extend outwardly from the tray above a few or many lower teeth 13, see FIG. 4

The placement of flexible bubbles 31 in FIGS. 3 and 4 depends on the individual's needs, preference, comfort, and/or dental issues. The mouth guard 10 or 30 can be made of semi-rigid or flexible polymer, a variety of plastic materials that can be adjusted or molded to one's mouth. The flexible bubbles 20 or 31 can be made with a bubble forming ball to create the air filled cavity 20 that protrudes out the upper or lower exterior surface of the mouth guard 10, and can range in size, shape and thickness. The purpose of the mouth guard 30 with protruding flexible bubbles 31 is to create a flexible barrier between the upper 12 and lower 13 front teeth or set of teeth to absorb shock, pressure when biting, or clenching and assist in preventing trauma, bruxism and TMJ.

While the invention has been explained by a detailed description of certain specific embodiments, it is understood that various modifications and substitutions can be made in any of them within the scope of the appended claims, which are intended also to include equivalents of such embodiments.

What is claimed is:

1. A mouthguard adapted to prevent teeth grinding and clenching of upper and lower posterior teeth by preventing contact by upper two to four front teeth against lower opposite teeth comprises:
    a tray having a substantially U-shaped channel including opposing spaced side walls and a base having a thickness adapted to fit over the upper teeth and mold to their configuration with imprints in the tray; and,
    a flexible bubble portion of the channel positioned around the upper two to four front teeth and extending downwardly and outwardly both anteriorly and posteriorly from the tooth imprints in the tray to prevent contact of the upper and lower opposite teeth and providing spacing between the upper and lower posterior teeth to prevent teeth grinding or clenching of the posterior teeth.

2. A mouthguard in accordance with claim 1 wherein:
    the mouthguard tray comprises a soft flexible elastic material adapted to mold to an individual's teeth and the bubble portion comprises a flexible polymer.

3. A mouthguard in accordance with claim 2 wherein:
    the tray material is a silicone rubber or an ultra-low density polyethylene and the flexible bubble portion includes an air-filled cavity.

4. A mouthguard adapted to prevent teeth grinding and clenching of upper and lower posterior teeth by preventing contact by lower two to four bottom front teeth against upper opposite teeth comprises:
    a tray having a substantially U-shaped channel including spaced side walls and a base having a thickness adapted to fit over the lower teeth and mold to their configuration with imprints in the tray; and,
    a flexible bubble portion of the channel positioned around the lower two to four front teeth and extending upwardly and outwardly both anteriorly and posteriorly from the tooth imprints in the tray to prevent contact of the upper and lower opposite teeth and providing spacing between the upper and lower posterior teeth to prevent teeth grinding or clenching of the posterior teeth.

\* \* \* \* \*